United States Patent [19]

Herrmann et al.

[11] Patent Number: 5,395,299

[45] Date of Patent: Mar. 7, 1995

[54] METHOD AND APPARATUS FOR TREATING A SUBJECT WITH FOCUSED ACOUSTIC WAVES

[75] Inventors: Klaus Herrmann, Nuremberg; Guenther Krauss, Erlangen, both of Germany

[73] Assignee: Siemens Aktiengesellschaft, Munich, Germany

[21] Appl. No.: 191,471

[22] Filed: Feb. 4, 1994

[30] Foreign Application Priority Data

Mar. 2, 1993 [DE] Germany ............... 43 06 460.4

[51] Int. Cl.⁶ ............................................. A61B 17/22
[52] U.S. Cl. ................................. 601/2; 128/660.01; 378/162; A61B/17/22
[58] Field of Search .......... 128/660.01, 660.03; 601/2, 4; 378/145, 146, 162

[56] References Cited

U.S. PATENT DOCUMENTS

| | | |
|---|---|---|
| 4,674,505 | 6/1987 | Pauli et al. . |
| 4,984,565 | 1/1991 | Rattner et al. . |
| 5,044,354 | 9/1991 | Goldhorn et al. . |
| 5,060,650 | 10/1991 | Wurster et al. ............... 128/660.03 |
| 5,070,861 | 12/1991 | Einars et al. ............................. 601/4 |

FOREIGN PATENT DOCUMENTS 0188750  7/1986  European Pat. Off. .
8714707  4/1989  Germany .

*Primary Examiner*—George Manuel
*Attorney, Agent, or Firm*—Hill, Steadman & Simpson

[57] ABSTRACT

A therapy apparatus has a source of acoustic waves which generates acoustic waves focused onto a focus and which has an x-ray-transparent region, and the focus lying in an isocenter and an x-ray locating system whose central ray proceeds through the isocenter and is adjustable relative to the source in a locating sequence such that a subject to be treated is irradiated by locating radiation from different directions, with the central ray in one of the irradiation directions proceeding through the x-ray transparent region and the acoustic wave source is maintained stationary during the sequence. A corresponding method is also disclosed.

43 Claims, 5 Drawing Sheets

METHOD AND APPARATUS FOR TREATING A SUBJECT WITH FOCUSED ACOUSTIC WAVES

BACKGROUND OF THE INVENTION

1. Field of the Invention

The present invention is directed to a therapy apparatus and method for treatment of a subject with focused acoustic waves, of the type wherein a source of acoustic waves generates acoustic waves focused onto a focus and has an x-ray-transparent region, and an x-ray locating means locates a region to be treated in the subject by obtaining an image of the subject from different irradiation directions and whose central ray in at least one transillumination direction proceeds through the x-ray-transparent region of the acoustic waves source.

2. Description of the Prior Art

Therapy systems of the type generally described above serve, for example, for treating stone conditions (lithotripsy), for treating tumors or for treating bone conditions (osteorestoration). In the former instance, a shockwave source is generally provided as the source of acoustic waves. In the case of treating tumors, a pressure pulse source that generates negative pressure pulses (under-pressure) and/or an ultrasound source that emits continuous ultrasound (hyperthermia) can, for example, be provided as the source of acoustic waves. For treating bone conditions, a shockwave source is likewise normally provided as the source of acoustic waves.

For example, European Application 0 372 119 discloses a therapy apparatus of the type initially described. In this known therapy apparatus, the source of acoustic waves is connected either to the primary radiation diaphragm of the x-ray radiator or to the image intensifier of the x-ray locating means. Acoustic coupling means in the form of a flexible foil are attached to the source of acoustic waves, this coupling means being capable of application to the body surface of a subject to be treated for the purpose of acoustic coupling. For locating a region to be treated, the source of acoustic waves and the x-ray locating means must be adjusted in common relative to the subject to be treated such that irradiation of the subject with x-rays ensues from two different directions. Relative motions and forces between the body surface of the subject to be treated and the coupling means pressing thereagainst necessarily occur. Quite apart from the fact that this can be uncomfortable for the subject to be treated, i.e., a patient, it involves the risk that the subject to be treated will be displaced in an uncontrolled fashion, so that the result of the locating procedure is imprecise. It is self-evident that an exact result can only be obtained when uncontrolled dislocations of the subject to be treated are avoided between the irradiation from different directions.

German Utility Model 87 14 701 discloses a shockwave generator having a central, x-ray-transparent region, but makes no mention of irradiation of the subject to be treated ensuing from different angles with an x-ray locating means. Successive irradiation from different angles, however, is not necessary since the x-ray-transparent region is dimensioned large enough such that irradiation from different angles can simultaneously ensue through the x-ray transparent region.

SUMMARY OF THE INVENTION

It is an object of the present invention to provide a therapy apparatus of the type initially described which avoids the risk that dislocation of the subject relative to the source of acoustic waves and, in particular, relative to the isocenter occur in an uncontrolled fashion in conjunction with the change in the irradiation direction of the x-ray locating means required for locating a region to be treated.

This object is achieved in a therapy apparatus and method for treatment with focused acoustic waves constructed in accordance with the principles of the present invention wherein a source of acoustic waves generates acoustic waves focused onto a focus and has an x-ray-transparent region, an x-ray locating means is enlarged for locating a region to be treated in subject to be treated which, in a locating sequence, irradiates the subject to be treated from different directions in succession for the purpose of locating, and wherein the x-ray locating means is adjustable relative to the acoustic waves source during locating such that its central ray for at least one irradiation direction per locating sequence proceeds through the x-ray-transparent region of the acoustic source and the source is maintained stationary during the locating sequence.

The x-ray locating means is adjusted relative to the source of acoustic waves in the manner required for changing the irradiation direction in the case of the therapy apparatus of the invention. This means that the source of acoustic waves, in contrast to known systems, is not moved relative to the subject to be treated when changing irradiation directions. The risk that dislocations of the subject relative to the source of acoustic waves and, in particular, relative to the isocenter occur in conjunction with the change of the transillumination direction is thus avoided.

When the x-ray locating means and the source are positioned relative to one another for irradiating the subject at a direction different from the direction wherein the useful beam proceeded through the acoustic waves source, the useful x-ray beam of the x-ray means proceeds at least essentially past (next to) the source. This assures that the image date acquired with the x-ray locating means in the second transillumination direction is not reduced to a noteworthy extent due to inclusion of an image of the source of acoustic waves in the x-ray image of the subject.

As noted above, in accordance with the invention the useful x-ray beam passes through the x-ray-transparent region of the source in at least one irradiation direction. In a further embodiment, the beam passes through the x-ray transparent region in only one irradiation direction and passes by the source in all other irradiation directions.

In order to be able to prepare x-ray exposures before, after and, if necessary, during the treatment for diagnostic purposes, which exposures are not deteriorated in any way by the presence of the source of acoustic waves in the beam path of the x-ray locating means, it is provided in an embodiment of the invention that the source is adjustable into a standby position in a known way as disclosed in European Application 0 405 282. The source is located outside the useful x-ray beam of the x-ray locating means in this standby position. It is self-evident that the focus of the focused acoustic waves is no longer located in the isocenter when the source of acoustic waves assumes its standby position. This, however, is insignificant since a generation of focused acoustic waves is not undertaken when the source assumes its standby position. Moreover, the acoustic coupling means that is seated against the subject to be treated in the operating position, i.e., when the focus of the acoustic waves is located in the isocenter, is not seated against the subject in the standby position, so that the acoustic waves cannot be coupled into the subject to be treated.

In order to be able to realize a compact structure of the therapy apparatus, the x-ray locating means in a version of the invention is pivotable around an axis proceeding parallel to the longitudinal axis of a support table provided for the subject to be treated. This can be realized in a technologically simple way when the x-ray locating means is attached to a C-arm in a known way as disclosed in European Application 0 405 282, this C-arm being pivotable around its center axis, which coincides with the longitudinal axis of the table.

A source carrier to which the source is attached and which is located outside the useful x-ray beam of the x-ray locating means can be provided in a known way as disclosed in European Application 0 405 282 in a further embodiment of the invention. Degradations of the x-ray images produced with the x-ray locating means due to the source carrier are thus precluded. The source carrier is preferably constructed with two arms such that the useful x-ray beam proceeds by and between the two arms of the source carrier when the focus of the acoustic waves is located in the isocenter. In this way, a stable holding of the source of acoustic waves can be realized without deteriorating the x-ray images produced with the x-ray locating means. The C-arm also preferably extends past and between the two arms of the source carrier. This assures a stable structure of the source carrier since angled portions, bends, etc., for avoiding the C-arm are avoided. As initially indicated, the radiation source of the x-ray locating means and the subject to be treated in a preferred embodiment are adjustable relative to one another. Such adjustment ensues first, in a direction that proceeds parallel to the direction of the central ray of the x-ray locating means and in a first irradiation direction, and second, in a direction that proceeds parallel to the direction of the central ray in a second irradiation direction. In this case, it is easily possible to position to a region to be treated on the central ray or on the acoustic axis with the assistance of the x-ray locating means.

In a further embodiment of the invention the adjustment of the source into and out of the standby position ensues on a straight line. A simple structure of the therapy apparatus is thereby achieved. When the adjustment of the source also ensues such that the acoustic axis of the source is dislocated in a plane that contains the central ray of the x-ray locating means, a further reduction of the structural outlay is achieved since articulations or the like which would otherwise be required in order to pivot the acoustic axis of the source into this plane can be eliminated.

Preferably, the focus lies in an isocenter and the central ray of the x-ray locating means proceeds through the isocenter, so that a region to be treated can be located especially easily.

DESCRIPTION OF THE PREFERRED EMBODIMENTS

Figure 1:
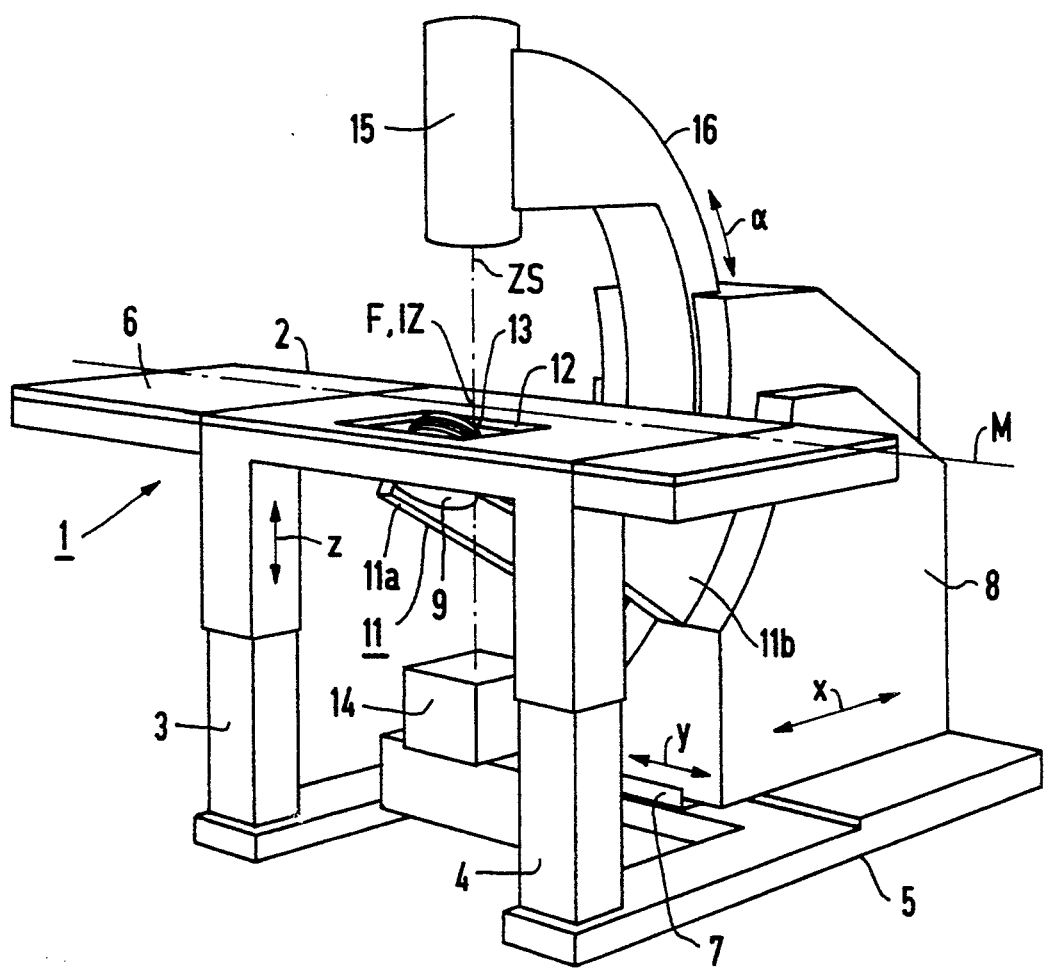
FIG. 1 shows a lithotripsy station of the invention in a perspective view.

As shown in FIG. 1, the therapy apparatus of the invention (operating according to the method of the invention) includes a support table generally referenced 1 as a bearing means for a subject to be treated. The bed plate 2 of the table 1 being height-adjustable relative to a base 5 by means of two telescoping columns 3 and 4. The bed plate 2, whose preferably horizontal upper side represents the bearing surface 6 for a patient to be treated, is height-adjustable in the direction of the double arrow z and, thus, parallel to the z-axis a Cartesian coordinate system, for which the x-axis and y-axis are also indicated.

A carriage 7 is seated on the base 5 for adjustment along a straight line in the direction of the longitudinal axis of the bed plate 2 which proceeds parallel to the y-axis of the spatial coordinate system, this being indicated by the double arrow referenced y.

A carrier generally referenced 8 is seated on the carriage 7 so as to be longitudinally displaceable in a direction proceeding transversely relative to the longitudinal axis of the bed plate 2 and, thus, parallel to the x-axis of the spatial coordinate system.

Movement-permitting support of the carriage 7 on the base 5 and of the carrier 8 on the carriage 7 ensues with known longitudinal guides that can be rolling bearings or plain bearings (not shown).

Thus the carrier 8 is adjustable relative to the bed plate 2 in a plane proceeding parallel to the seating surface 6 and the bed plate 2 is adjustable relative to the carrying part 8 in a direction that proceeds at a right angle relative to this plane. The adjustment of the carrier 8, the carriage 7 and of the bed plate 2 in the direction of the double arrows x, y, z ensues by motor drive (not shown) employing suitable motors, particularly electric motors, and suitable gearings such as mechanical gearings, as needed.

The therapy apparatus also includes a source 9 of focused acoustic waves which may be, for example, an electromagnetic shockwave source of the type disclosed in European Application 0 372 119. The source 9 thus has a central x-ray-transparent region formed by an opening 10 (see FIG. 2 and 3) and through which the acoustic axis A of the source 9 proceeds. The focus F of the acoustic waves generated by the source 9 lies on the acoustic axis A. Further details with respect to electromagnetic shockwave sources can be found in the disclosures of U.S. Pat. No. 4,674,505 and European Application 0 188 750, the teachings of which are incorporated herein by reference.

Figure 2:
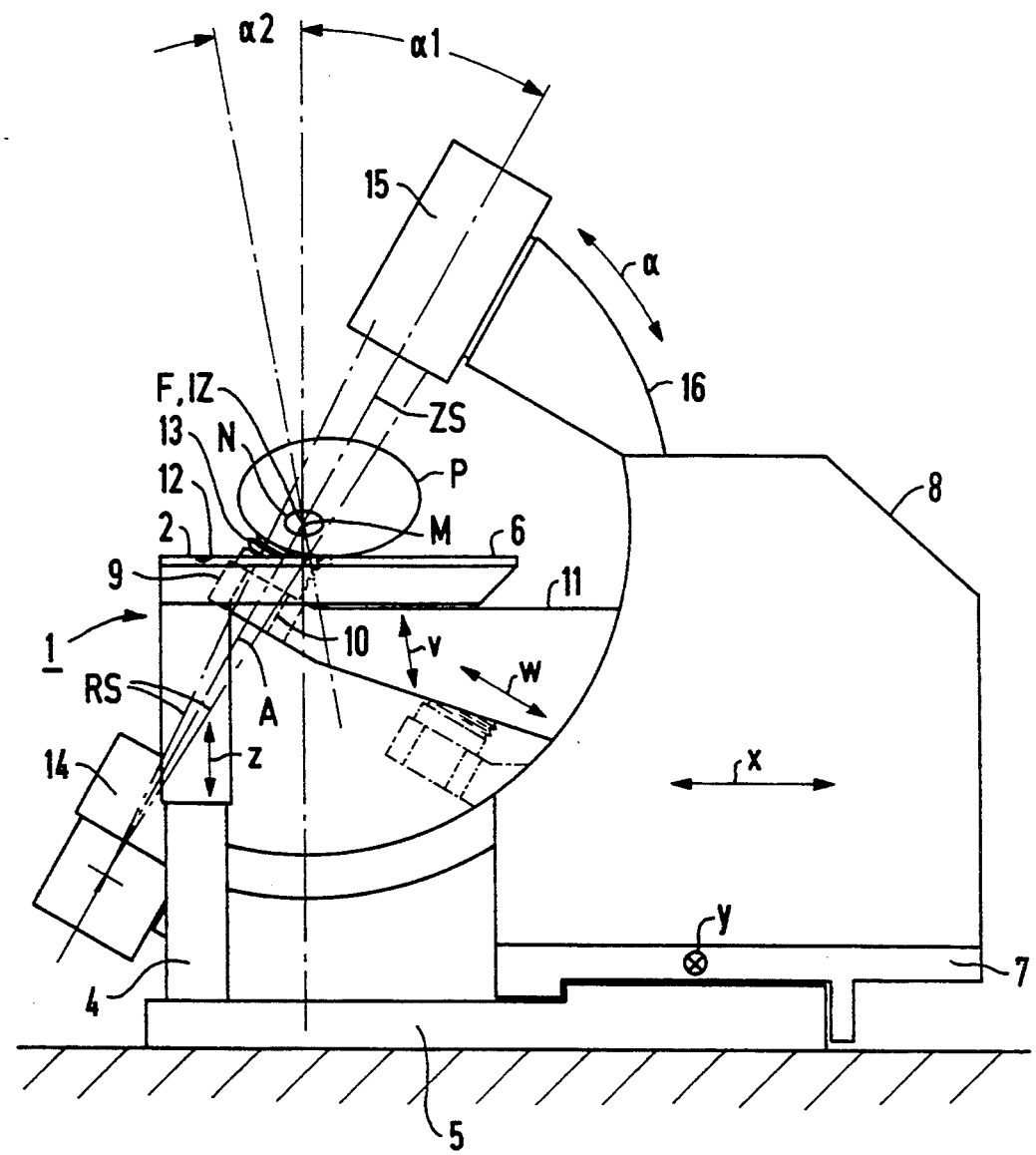
FIG. 2 and 3 respectively show front views of the lithotripsy station of FIG. 1 in different operating conditions.

The source 9 is attached to a source carrier 11 that is in turn attached longitudinally displaceably to the carrier 8 such that the source 9—proceeding from a standby position indicated with broken lines in FIG. 2—can be adjusted on a straight line in the direction of the double arrow w into its working position shown in FIG. 1, which is shown with solid lines in FIG. 2.

When the source 9 assumes its working position, the focus F is situated in an isocenter IZ above the bearing surface 6 of the bed plate 2. The acoustic axis A of the source 9 then extends through the isocenter IZ. The source 9 has a flexible, bellow-like coupling cushion 13 which forms the coupling means required for the acoustic coupling to a subject to be treated. In the working position, this cushion projects through an opening 12 of the bed plate 2.

An x-ray locating means is also attached to the carrier 8, which includes on x-ray radiator 14 and an x-ray image intensifier 15 disposed opposite each other. These are attached to the ends of an arcuately curved C-arm 16. The C-arm is adjustably attached to the carrier 8 along the circumference thereof in the direction of the curved double arrow $a$. Stated more precisely, the C-arm 16 is pivotable around its center axis M. The central ray ZS of the x-ray beam (defined by edge rays RS) of the x-ray locating means intersects the center axis M of the C-arm at a right angle. The C-arm 16, moreover, is attached such to the carrier 8 such that the center axis M of the C-arm 16 and the central ray ZS proceed through the isocenter IZ. It is thus assured that the central ray ZS of the x-ray locating beam proceeds through the isocenter IZ for any desired pivoted positions of the C-arm 16. The source 9, moreover, is attached such to the source carrier 11 such that the acoustic axis A and the central ray ZS lie in a common plane when the source 9 assumes its working position. It is also provided in this exemplary embodiment that the adjustment motion of the source 9 from its standby position into its working position and vice versa ensues such that the acoustic axis A and the central ray ZS always lie in a common plane. The adjustment of the source 9 from its standby position into its working position and vice versa in the direction of the double arrow w, as well as the pivoting of the C-arm 16 in the direction of the double arrow $a$, ensue by motor-drive (not shown), preferably electromotively and upon employing of suitable gearings as required.

Figure 3:
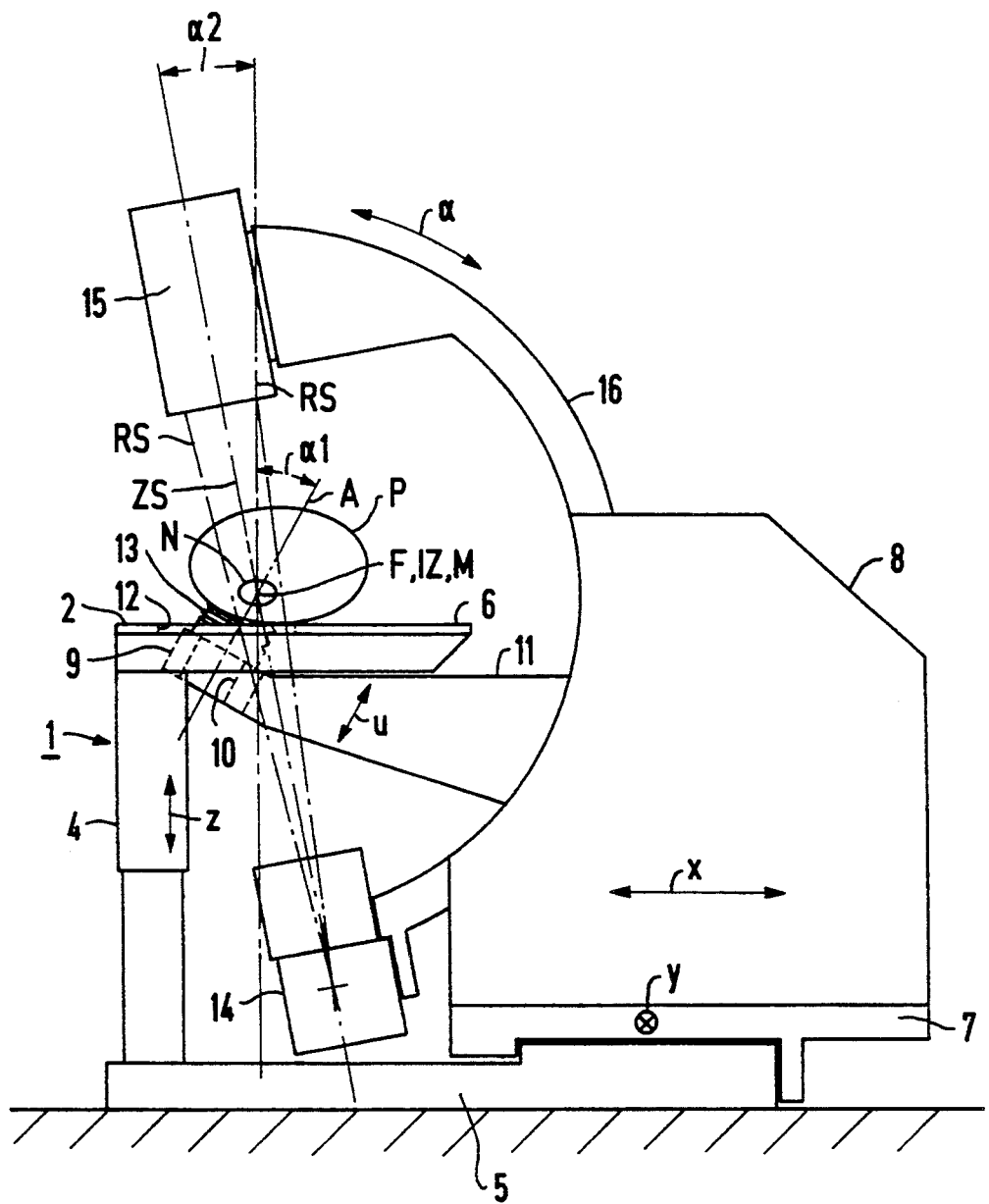

A patient is schematically shown in section in FIGS. 2 and 3 as the examination subject. In order to spatially locate a region to be treated, for example, a kidney stone in the kidney N of the patient P, using the x-ray locating means and to be able to displace the locating means into the isocenter IZ, and into the focus F of the source 9 in its working position, the patient P is irradiated in succession from two different directions with the x-ray locating means. The resulting data are analyzed in a known way in order to be able to obtain the required information about the spatial position of the kidney stone. The position of the x-ray locating means and of the source 9 relative to one another corresponding to the first irradiation direction is shown in FIG. 2. The C-arm 16 consequently assumes a position for the first irradiation direction wherein the central ray ZS proceeds in a first direction and intersects the vertical at an angle $a1$ of, for example, $+30°$. In this position, the central ray ZS of the x-ray locating means and the acoustic axis A of the source 9 in its working position coincide. Consequently, the useful x-ray beam proceeds through the x-ray-transparent region of the source 9 formed by the opening 10. The position of the x-ray locating means and of the source 9 relative to one another corresponding to the second irradiation direction is shown in FIG. 3. In this position, the central ray ZS proceeds in a second direction wherein it intersects the vertical at an angle $a2$ of, for example, $-10°$. The useful x-ray beam essentially passes by (next to) the source 9 in this position. Only a slight part of the x-ray beam is incident on the source 9, so that no serious degradation of the image data available in the first irradiation direction occurs. In its standby position, moreover, the source 9 is situated entirely outside the useful x-ray beam.

For reasons explained below, the drives for the height adjustment of the bed plate 2 in the direction of the z-axis and the adjustment of the carrier 8 in the direction of the X-axis when the C-arm is situated in the first and in the second irradiation directions are synchronized with one another such that the two drives can be actuated only in common, at least during a fine-locating event described below. The common adjustment is such that a resulting motion of the region to be treated and of the isocenter IZ relative to one another for the first irradiation direction occurs parallel to the direction of the central ray ZS in the second irradiation direction, and occurs in the second irradiation direction parallel to the direction of the central ray ZS in the first irradiation direction. The directions of these relative motions are indicated in FIGS. 2 and 3 by the double arrows respectively referenced v and u. This is achieved by selecting the adjustment speeds in the x-direction and the z-direction such that the quotient of speed in the x-direction and the speed in z-direction for the first irradiation direction is equal to $\tan a2$, and is equal to $\tan a1$ for the second irradiation direction.

For implementing a treatment, one proceeds by first bringing the source 9 into its standby position. The patient P then gets onto the bed plate 2 or is placed on the bed plate 2 by the attending personnel. It is self-evident that the patient P assumes a position wherein the region to be treated is located above the opening 12 of the bed plate 2.

A rough locating is subsequently undertaken, the source 9 thereby remaining in its standby position. For rough locating, the patient is first irradiated with the x-ray locating means in the first irradiation direction (angle $a1$ between central ray 25 and vertical). The carrier 8 is adjusted in the direction of the x-axis and the y-axis such that the image of the region to be treated coincides with a mark in the x-ray image displayed on a monitor, this mark corresponding in a known way to the projection of the isocenter IZ into the image plane of the x-ray image. When the carrier 8 is aligned in the described way, the region to be treated lies on the central ray ZS proceeding in the direction corresponding to the first irradiation direction.

The C-arm 16 is then pivoted to the second irradiation direction (angle $a2$ between central ray 25 and vertical). The patient is then again irradiated and the image of the region to be treated in the x-ray image displayed on the monitor is brought into coincidence with the mark by a synchronous drive (ensuing in the way set forth above) of the drives for the support plate 2 in the direction of the z-axis and the carrier 8 in the direction of the x-axis. The relative motion between the isocenter IZ and the region to be treated thus ensues in the u-direction.

The preliminary locating has thus been completed. The region to be treated is located in the isocenter IZ. The source 9 is now brought from its standby position into its working position wherein it presses against the body surface of the patient P with the coupling cushion 13. The slight dislocation of the region to be treated from the isocenter IZ and, thus, from the focus F of the source 9 which may possibly occur as a result thereof is corrected by a fine locating procedure.

To this end, the x-ray locating means is first activated again in the second irradiation direction and the image of the region to be treated is, if necessary, brought into coincidence with the mark by adjusting the region to be treated and by adjusting the isocenter IZ and the focus F relative to one another in u-direction. The central ray ZS proceeding in the second direction then proceeds through the region to be treated. The C-arm 16 is now adjusted back to the first irradiation direction, the useful x-ray beam now proceeding through the opening 10 of the source 9 therein since the source 9 is now in its working position. As necessary, the image of the region to be treated is brought into coincidence with the mark on the basis of synchronous drive of the drives for the bed plate 2 in the direction of the z-axis and the carrier 8 in the direction of the x-axis. This occurs on the basis of a relative motion between the region to be treated and the isocenter IZ and the focus F, this relative motion ensuing in the v-direction. The region to be treated is now also located in the focus F with the source 9 applied to the patient P.

Figure 4:
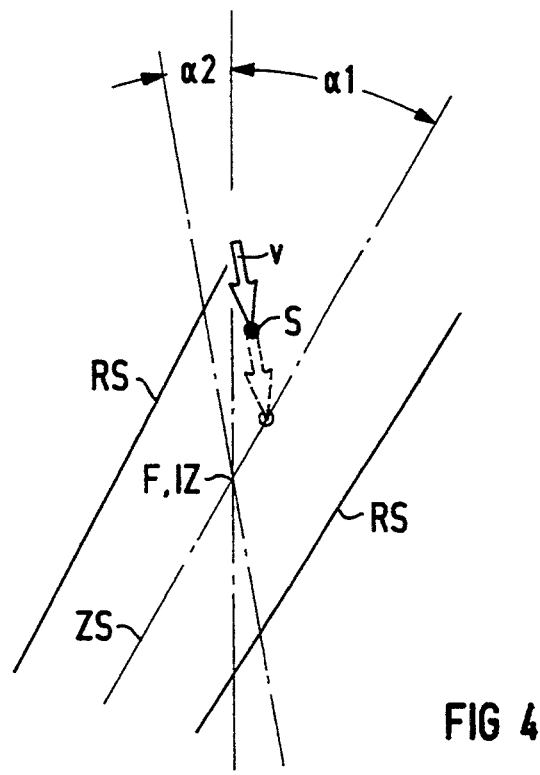
FIG. 4 and 5 are respective schematic diagrams for illustrating apparatus movements for the operating conditions according to FIG. 2 and 3.
Figure 5:
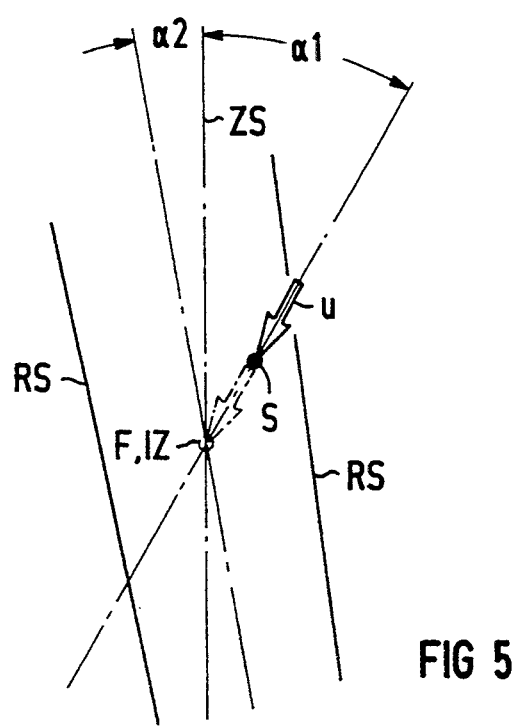

The fine locating procedure is shown again in FIGS. 4 and 5. The left part of FIG. 4 shows how—for the first irradiation direction—a region to be treated, for example, a stone S in a kidney, is brought into a position on a basis of motion in the v-direction, i.e., parallel to the second direction (angle $\alpha 2$) of the central ray ZS, such that it lies on the central ray ZS proceeding in the first direction (angle $\alpha 1$). For the case of the second irradiation direction, FIG. 5 shows how the kidney stone S is positioned onto the central ray ZS proceeding in the central direction (angle $\alpha 2$), and is thus moved, into the isocenter IZ, by motion in the u-direction parallel to the first direction (angle $\alpha 1$) of the central ray ZS.

After the region to be treated and the isocenter IZ—which corresponds to the position of the focus F of the acoustic waves—have been brought into coincidence in the above-described way, one can begin charging the region to be treated with acoustic waves.

The bearing support 1, the carriage 7 and the carrier 8 interact with one another to form a positioning means with which the region to be treated and the focus F are adjustable relative to one another such that the focus F is located in the region to be treated. The drives allocated to the support table 1 to the carriage 7 and to the carrier 8 for adjustment in the z-direction, in the y-direction and in the x-direction form adjustment means with which the region to be treated and the focus F are adjustable relative to one another in the first adjustment direction (such as the y-direction) that intersects the plane containing the central ray ZS of the x-ray locating means for both irradiation directions, and in a second adjustment direction (such as the x-direction) contained in this plane as well as in a third adjustment direction (such as the z-direction) differing from the first and second directions. The adjustment means can be actuated synchronously with one another with respect to the second and third adjustment directions, (the x-direction and the z-direction) such that, as set forth above, a relative motion between the region to be treated and the focus F occurs whose direction u or v proceeds parallel to the respective first or second direction $\alpha 1$ or $\alpha 2$ of the central ray ZS. In this way, it is possible to quickly locate a region to be treated and to position it in a way required for the treatment, even though neither the first nor the second direction $\alpha 1$ or $\alpha 2$ of the central ray ZS coincides with one of the adjustment directions, namely the x-direction, the y-direction or the z-direction.

As mentioned, the source 9 can be a generator of a focused shockwaves. In addition to kidney stones, bone conditions can also be treated with such a shockwave source. However, a pressure pulse source as disclosed, for example, in German Utility Model 91 09 025 can alternatively be provided as the source 9. Such a source generates negative pressure pulses and is particularly suited for treating tumors. Further, a therapeutic ultrasound source can be provided as the source 9, emitting therapeutic ultrasound as continuous sound for treating tumors. Further, sources as disclosed in U.S. Pat. Nos. 4,926,857 and 4,976,255 which combine a pressure pulse source and a therapeutic ultrasound source, can be provided as the source 9, for example, for treating tumors.

Regardless of the source 9 that is employed, there is the possibility of integrating an ultrasound locating unit therein in a known way, this ultrasound locating unit being potentially fashioned in a known way either with an ultrasound B-scanner or with an ultrasound echo locating means (A-scan). There is the possibility in the case of an ultrasound B-scanner of inserting the scanner (applicator) into the opening 19 of the source 9 for undertaking the ultrasound locating.

Figure 6:
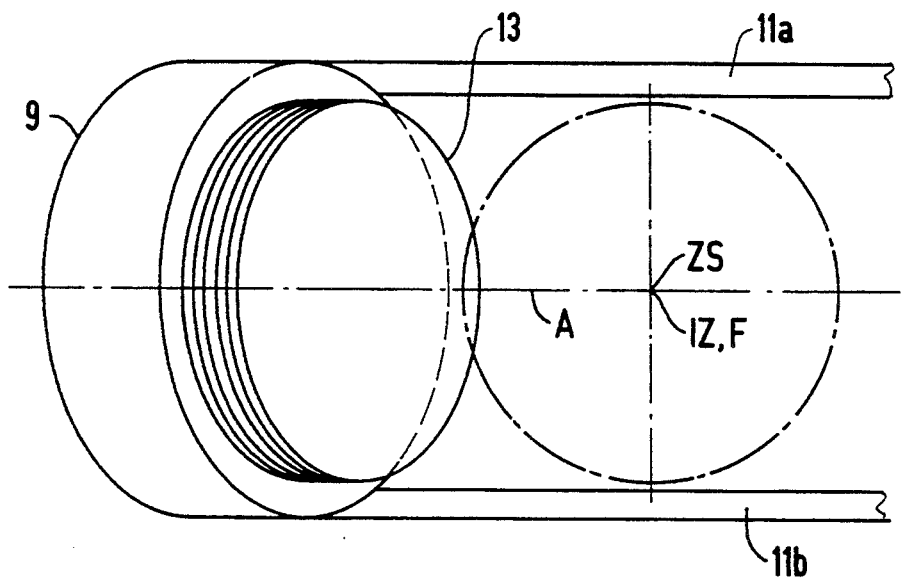
FIG. 6 shows a more detailed view of a portion of the lithotripsy station according to FIG. 1 through 3.

As may be seen from FIG. 6, the source carrier 11 is implemented with two arms. Both in the working position of the source shown in FIG. 6 and in the standby position thereof (which is indicated with broken lines in FIG. 2), its arms 11a and 11b are located outside the useful x-ray beam of the x-ray locating means whose cross-section is indicated with shading in FIG. 6. The useful x-ray beam thereby passes between the arms 11a and 11b when the source 9 is in its working position.

The therapy apparatus of the invention has the advantage that the x-ray locating means can be adjusted from its first into its second irradiation direction independently of the source of acoustic waves. The relative motions between source and patient are thus limited to those relative motions that are in fact required in order to bring the region to be treated into the isocenter or into the focus of the source, possibly after undertaking a preliminary positioning. Dislocations of the patient relative to the source that are caused by changing the transillumination direction thus do not occur.

It is not necessary during the locating procedure to constantly irradiate the patient with the x-ray locating means. On the contrary, the locating procedure can largely ensue on the basis of stored x-ray images, referred to as "stored shots," in a known way.

In the exemplary embodiment that has been set forth, the central ray of the x-ray locating means does not proceed parallel to one of the adjustment directions, x-direction, y-direction and z-direction, either in the first or the second irradiation directions. Alignment of the central ray with one of these axes, however, is within the framework of the invention.

Although modifications and changes may be suggested by those skilled in the art, it is the intention of the inventors to embody within the patent warranted hereon all changes and modifications as reasonably and properly come within the scope of their contribution to the art.

We claim as our invention:

1. An apparatus for treating a subject with focused acoustic waves comprising:
    source means for generating acoustic waves converging at a focus, having an x-ray transparent region;

x-ray transparent coupling means, directly applicable to a subject to be treated with said acoustic waves, for coupling said acoustic waves into said subject;

x-ray locating means, including a single x-ray source, for locating a region in said subject to be treated with said acoustic waves by, in a locating sequence, successively irradiating said subject with a useful x-ray beam from a plurality of different directions; and means for adjusting the position of said locating means relative to said source means during said locating sequence for causing said useful x-ray beam to pass through said x-ray transparent region of said source means in at least one of said irradiation directions while maintaining said source means stationary during said locating sequence.

2. An apparatus as claimed in claim 1 wherein said means for adjusting the position of said locating means comprises means for positioning said locating means for causing said useful x-ray beam to pass by said source means in at least one of said irradiation directions.

3. An apparatus as claimed in claim 1 further comprising means for adjusting the position of said source means for moving said source means to a standby position, when said locating sequence is not being conducted, wherein said source means is disposed outside of said useful x-ray beam.

4. An apparatus as claimed in claim 1 further comprising:
a support table for supporting said subject to be treated with acoustic waves, said support table having a longitudinal axis, and wherein said means for adjusting the position of said locating means comprises means for pivoting said x-ray locating means around an axis extending parallel to said longitudinal axis of said support table.

5. An apparatus as claimed in claim 4 wherein said means for adjusting the position of said locating means includes a C-arm carrying said x-ray locating means, said C-arm having a center axis about which said C-arm is rotatable, said center axis coinciding with said axis extending parallel to said longitudinal axis of said support table.

6. An apparatus as claimed in claim 1 further comprising carrier means for supporting said source means, said carrier means being disposed outside of said useful x-ray beam of said x-ray locating means.

7. An apparatus as claimed in claim 6 wherein said apparatus has an isocenter, and wherein said carrier means comprises two arms respectively attached to said source means and disposed so that said useful x-ray beam proceeds between said two arms when said focus of said acoustic waves is located in said isocenter.

8. An apparatus as claimed in claim 7 wherein said means for adjusting the position of said locating means includes a C-arm carrying said x-ray locating means, and wherein said C-arm extends between said two arms of said carrier means.

9. An apparatus as claimed in claim 8 further comprising:
a support table for supporting said subject to be treated with acoustic waves, said support table having a longitudinal axis, and wherein said means for adjusting the position of said locating means comprises means for pivoting said x-ray locating means around an axis extending parallel to said longitudinal axis of said support table.

10. An apparatus as claimed in claim 9 wherein said means for adjusting the position of said locating means includes a C-arm carrying said x-ray locating means, said C-arm having a center axis about which said C-arm is rotatable, said center axis coinciding with said axis extending parallel to said longitudinal axis of said support table.

11. An apparatus as claimed in claim 1 wherein said useful x-ray beam has a central ray and wherein said means for adjusting the position of said locating means comprises means for adjusting the position of said locating means and the position of said source, and for adjusting the position of said subject, in a first direction proceeding parallel to said central ray in a first of said irradiation directions and in a second direction proceeding parallel to said central ray in a second of said irradiation directions.

12. An apparatus as claimed in claim 1 further comprising means for moving said source means in a straight line between a standby position outside of said useful x-ray beam and a working position, during said locating sequence, wherein said source means is applied against said subject.

13. An apparatus as claimed in claim 12 wherein said source means has an acoustic axis and wherein said useful x-ray beam of said locating means has a central ray, and wherein said means for moving said source means between said standby position and said working position comprises means for moving said source means for displacing said acoustic axis in a plane containing said central ray.

14. An apparatus as claimed in claim 1 wherein said apparatus has an isocenter, wherein said useful x-ray beam of said locating means has a central ray, wherein said source means comprises means for generating acoustic waves converging at a focus located at said isocenter, and wherein said locating means comprises means for locating a region in said subject to be treated with said acoustic waves by, in a locating sequence, successively irradiating said subject with a useful ray beam with said central ray proceeding through said isocenter from a plurality of different directions.

15. An apparatus as claimed in claim 1 further comprising:
a support table for supporting said subject to be treated with acoustic waves, said support table having a longitudinal axis, and wherein said means for adjusting the position of said locating means comprises means for pivoting said x-ray locating means around an axis extending parallel to said longitudinal axis of said support table.

16. An apparatus as claimed in claim 15 wherein said means for adjusting the position of said locating means includes a C-arm carrying said x-ray locating means, said C-arm having a center axis about which said C-arm is rotatable, said center axis coinciding with said axis extending parallel to said longitudinal axis of said support table.

17. An apparatus as claimed in claim 1 wherein said source means further comprises coupling means, directly applicable to a subject to be treated with said acoustic waves, for coupling said acoustic waves into said subject.

18. An apparatus for treating a subject with focused acoustic waves comprising:
source means for generating acoustic waves converging at a focus, having an x-ray transparent region;

x-ray transparent coupling means, directly applicable to a subject to be treated with said acoustic waves, for coupling said acoustic waves into said subject;

x-ray locating means, including a single x-ray source, for locating a region in said subject to be treated with said acoustic waves by, in a locating sequence, successively irradiating said subject with a useful x-ray beam from a plurality of different directions; and means for adjusting the position of said locating means relative to said source means during said locating sequence for causing said useful x-ray beam to pass through said x-ray transparent region of said source means in only one of said irradiation directions while maintaining said source means stationary during said locating sequence.

19. An apparatus as claimed in claim 18 wherein said means for adjusting the position of said locating means comprises means for positioning said locating means for causing said useful x-ray beam to pass by said source means in at least one of said irradiation directions.

20. An apparatus as claimed in claim 18 further comprising means for adjusting the position of said source means for moving said source means to a standby position, when said locating sequence is not being conducted, wherein said source means is disposed outside of said useful x-ray beam.

21. An apparatus as claimed in claim 18 further comprising carrier means for supporting said source means, said carrier means being disposed outside of said useful x-ray beam of said x-ray locating means.

22. An apparatus as claimed in claim 21 wherein said apparatus has an isocenter, and wherein said carrier means comprises two arms respectively attached to said source means and disposed so that said useful x-ray beam proceeds between said two arms when said focus of said acoustic waves is located in said isocenter.

23. An apparatus as claimed in claim 22 wherein said means for adjusting the position of said locating means includes a C-arm carrying said x-ray locating means, and wherein said C-arm extends between said two arms of said carrier means.

24. An apparatus as claimed in claim 23 further comprising:

a support table for supporting said subject to be treated with acoustic waves, said support table having a longitudinal axis, and wherein said means for adjusting the position of said locating means comprises means for pivoting said x-ray locating means around an axis extending parallel to said longitudinal axis of said support table.

25. An apparatus as claimed in claim 24 wherein said means for adjusting the position of said locating means includes a C-arm carrying said x-ray locating means, said C-arm having a center axis about which said C-arm is rotatable, said center axis coinciding with said axis extending parallel to said longitudinal axis of said support table.

26. An apparatus as claimed in claim 18 wherein said useful x-ray beam has a central ray and wherein said means for adjusting the position of said locating means comprises means for adjusting the position of said locating means and the position of said source, and for adjusting the position of said subject, in a first direction proceeding parallel to said central ray in a first of said irradiation directions and in a second direction proceeding parallel to said central ray in a second of said irradiation directions.

27. An apparatus as claimed in claim 18 further comprising means for moving said source means in a straight line between a standby position outside of said useful x-ray beam and a working position, during said locating sequence, wherein said source means is applied against said subject.

28. An apparatus as claimed in claim 27 wherein said source means has an acoustic axis and wherein said useful x-ray beam of said locating means has a central ray, and wherein said means for moving said source means between said standby position and said working position comprises means for moving said source means for displacing said acoustic axis in a plane containing said central ray.

29. A method as claimed in claim 28 comprising the additional step of:

causing said useful x-ray beam of said locating means to pass by said acoustic wave source in one of said irradiation directions.

30. A method for treating a subject with focused acoustic waves comprising:

generating acoustic waves, from an acoustic wave source having an x-ray transparent region, converging at a focus for treating a subject with said acoustic waves;

locating a region in said subject to be treated with said acoustic waves using an x-ray locating means by, in a locating sequence, successively irradiating said subject with a useful x-ray beam from a single x-ray source from a plurality of different directions;

adjusting the position of said locating means relative to said acoustic wave source during said locating sequence for causing said useful x-ray beam to pass through said x-ray transparent region of said acoustic wave source in at least one of said irradiation directions; and maintaining said acoustic wave source acoustically coupled to said subject via an x-ray transparent coupling means in direct contact with said subject at a stationary location during said locating sequence.

31. A method as claimed in claim 30 comprising the additional step of:

moving said acoustic wave source to a standby position outside of said useful x-ray beam when said locating sequence is not being conducted.

32. A method as claimed in claim 30 comprising the additional steps of:

supporting said subject on a support table having a longitudinal axis; and pivoting said x-ray locating means around an axis extending parallel to said longitudinal axis of said support table for irradiating said subject from said different directions.

33. A method as claimed in claim 30 wherein said useful x-ray beam has a central ray, and wherein the step of adjusting the position of said locating means is further defined by adjusting the position of said locating means relative to said subject in a first direction extending parallel to said direction of said central ray in a first of said irradiation directions and adjusting said locating means in a second direction proceeding parallel to said central ray in a second of said irradiation directions.

34. A method as claimed in claim 30 comprising the additional step of:

moving said acoustic wave source along a straight line between a standby position, wherein said acoustic wave source is outside of said useful x-ray beam, to a working position, wherein said acoustic wave source is in direct contact with said subject.

35. A method as claimed in claim 34 wherein said acoustic wave source has an acoustic axis and wherein said useful x-ray beam has a central ray, and wherein the step of moving said acoustic wave source between said standby position and said working position is further defined by moving said acoustic wave source for displacing said acoustic axis in a plane containing said central ray.

36. A method as claimed in claim 35 comprising the additional step of:
    causing said useful x-ray beam of said locating means to pass by said acoustic wave source in one of said irradiation directions.

37. A method for treating a subject with focused acoustic waves comprising:
    generating acoustic waves, from an acoustic wave source having an x-ray transparent region, converging at a focus for treating a subject with said acoustic waves;
    locating a region in said subject to be treated with said acoustic waves using an x-ray locating means by, in a locating sequence, successively irradiating said subject with a useful x-ray beam from a single x-ray source from a plurality of different directions;
    adjusting the position of said locating means relative to said acoustic wave source during said locating sequence for causing said useful x-ray beam to pass through said x-ray transparent region of said acoustic wave source in only one of said irradiation directions; and
    maintaining said acoustic wave source acoustically coupled to said subject via an x-ray transparent coupling means in direct contact with said subject at a stationary location during said locating sequence.

38. A method as claimed in claim 37 comprising the additional step of:
    moving said acoustic wave source to a standby position outside of said useful x-ray beam when said locating sequence is not being conducted.

39. A method as claimed in claim 37 comprising the additional steps of:
    supporting said subject on a support table having a longitudinal axis; and
    pivoting said x-ray locating means around an axis extending parallel to said longitudinal axis of said support table for irradiating said subject from said different directions.

40. A method as claimed in claim 37 wherein said useful x-ray beam has a central ray, and wherein the step of adjusting the position of said locating means is further defined by adjusting the position of said locating means relative to said subject in a first direction extending parallel to said direction of said central ray in a first of said irradiation directions and adjusting said locating means in a second direction proceeding parallel to said central ray in a second of said irradiation directions.

41. A method as claimed in claim 37 comprising the additional step of:
    moving said acoustic wave source along a straight line between a standby position, wherein said acoustic wave source is outside of said useful x-ray beam, to a working position, wherein said acoustic wave source is in direct contact with said subject.

42. A method as claimed in claim 40 wherein said acoustic wave source has an acoustic axis and wherein said useful x-ray beam has a central ray, and wherein the step of moving said acoustic wave source between said standby position and said working position is further defined by moving said acoustic wave source for displacing said acoustic axis in a plane containing said central ray.

43. An apparatus for treating a subject with focused acoustic waves comprising:
    source means for generating acoustic waves converging at a focus, said source means having an x-ray transparent region;
    x-ray transparent coupling means, directly applicable to a subject to be treated with said acoustic waves, for coupling said acoustic waves into said subject;
    x-ray locating means for locating a region in said subject to be treated with said acoustic waves by, in a locating sequence, successively irradiating said subject with a useful x-ray beam from a plurality of different directions; and
    means for adjusting the position of said locating means relative to said source means during said locating sequence for causing said useful x-ray beam to pass
    through said x-ray transparent region of said source means in a first one of said irradiating directions and to pass by, at least substantially, said source means in a second one of said irradiation positions.

* * * * *